(12) United States Patent
Park et al.

(10) Patent No.: US 11,795,304 B2
(45) Date of Patent: Oct. 24, 2023

(54) NITROCELLULOSE MEMBRANE COMPRISING NON-COVALENTLY ATTACHED ORGANIC NANOSTRUCTURED MOLECULE

(71) Applicant: NB Postech, Anyang-si (KR)

(72) Inventors: Joon Won Park, Pohang-si (KR); Sung Min Seo, Incheon (KR)

(73) Assignee: NB Postech, Anyang-si (KR)

( * ) Notice: Subject to any disclaimer, the term of this patent is extended or adjusted under 35 U.S.C. 154(b) by 725 days.

(21) Appl. No.: 16/960,021

(22) PCT Filed: Nov. 1, 2018

(86) PCT No.: PCT/IB2018/058584
§ 371 (c)(1),
(2) Date: Jul. 3, 2020

(87) PCT Pub. No.: WO2020/089678
PCT Pub. Date: May 7, 2020

(65) Prior Publication Data
US 2021/0230399 A1 Jul. 29, 2021

(51) Int. Cl.
*C08L 1/18* (2006.01)
*B01D 67/00* (2006.01)
(Continued)

(52) U.S. Cl.
CPC ............ *C08L 1/18* (2013.01); *B01D 67/0088* (2013.01); *B01D 71/20* (2013.01); *G01N 33/54393* (2013.01)

(58) Field of Classification Search
CPC ....... C08L 1/18; B01D 67/0088; B01D 71/20; G01N 33/54393
(Continued)

(56) References Cited

U.S. PATENT DOCUMENTS

2009/0048120 A1* 2/2009 Park ..................... G01Q 60/42
506/9
2016/0222442 A1* 8/2016 Cary ................... G01N 33/523

FOREIGN PATENT DOCUMENTS

WO   WO 2008/044896 A1   4/2008
WO   WO-2008044896 A1 *  4/2008   ............. B82Y 30/00
(Continued)

OTHER PUBLICATIONS

Hong et al. "Nanoscale-Controlled Spacing Provides DNA Microarrays with the SNP Discrimination Efficiency in Solution Phase", Langmuir, 2005, vol. 21, 4257-4261 (Year: 2005).*
(Continued)

*Primary Examiner* — Michael M. Bernshteyn
(74) *Attorney, Agent, or Firm* — Don D. Cha; HDC Intellectual Property Law, LLP

(57) ABSTRACT

The present invention provides an improved method of quantitative and/or qualitative analysis of a target molecule using nitrocellulose membrane (NCM). In particular, the present invention provides a porous nitrocellulose membrane that includes a surface and an organic nanostructured molecule that is non-covalently attached to the surface of NCM. The organic nanostructured molecule has a branched region that includes a plurality of terminal region (e.g., terminal end) moieties that are non-covalently attached or bound to a surface of the porous NCM. The organic nanostructured molecule also comprises a linear region that includes a covalently attached capture molecule that is adapted to selectively bind to a target molecule. The NCM of the invention provides an improved reproducibility, reliability, and selectivity compared an NCM in the absence of the organic nanostructured molecule.

18 Claims, 7 Drawing Sheets

(51) Int. Cl.
*B01D 71/20* (2006.01)
*G01N 33/543* (2006.01)

(58) Field of Classification Search
USPC .......................................................... 524/716
See application file for complete search history.

(56) References Cited

FOREIGN PATENT DOCUMENTS

| WO | WO 2009/005552 A2 | 1/2009 | |
|----|----|----|----|
| WO | WO-2009005552 A2 * | 1/2009 | ............ B01L 3/5023 |
| WO | WO 2011/072290 A2 | 6/2011 | |
| WO | WO2017138946 A1 | 8/2017 | |
| WO | WO 2018/140953 A1 | 8/2018 | |

OTHER PUBLICATIONS

Hong, B.J. et al., Langmuir, 2005, vol. 21, No. 10, pp. 4257-4261.
Dilip K Tosh et al., Bioconjugate. Chem., 2010, vol. 10, No. 2, pp. 372-384.

* cited by examiner

NITROCELLULOSE MEMBRANE COMPRISING NON-COVALENTLY ATTACHED ORGANIC NANOSTRUCTURED MOLECULE

CROSS-REFERENCE TO RELATED APPLICATIONS

This application is a 35 U.S.C. § 371 U.S. National Stage Application of PCT Patent Application No. PCT/IB2018/058584, filed Nov. 1, 2018, which is incorporated herein by reference in its entirety.

FIELD OF THE INVENTION

The present invention relates to a porous nitrocellulose membrane that includes a surface and an organic nanostructured molecule and a method for producing and using the same. In particular, the porous NCM of the invention includes a surface bound organic nanostructured molecule. The organic nanostructured molecule has a branched region that includes a plurality of terminal region (e.g., terminal end) moieties that are non-covalently attached or bound to a surface of the porous NCM. The organic nanostructured molecule also comprises a linear region that includes a covalently attached capture molecule that is adapted to selectively bind to a target molecule.

BACKGROUND OF THE INVENTION

The nitrocellulose membrane is a porous membrane composed of nitrocellulose. Porous nitrocellulose membranes typically have a median pore size diameter ranging from about 0.2 µm to about 15 µm. While nitrocellulose membranes are overall neutral, they have been used in immobilizing proteins via a strong dipole moment between the nitro group of the NCM and a dipole moment that is present in the protein. In some instances, ionic side chains of the protein have also been used to immobilize proteins on the NCM. The ability of NCMs in immobilizing proteins vary with the pH of the solution used. Without being bound by any theory, it is believed that the pH affects the immobilization efficiency of a particular protein by altering the properties of the protein in solution.

Nitrocellulose membranes have also been used to electrostatically immobilize nucleic acids. Relative to double-stranded DNA, nitrocellulose has a particularly high affinity for single-stranded DNA and DNA-RNA hybrids. Typically, NCMs do not immobilize RNA. These differences in nucleotide binding properties have been used to separate or quantify a single strand nucleotide chain and a single chain nucleic acid in a liquid phase hybrid formation reaction, and to separate or quantify a nucleic acid that forms a complex with a protein.

For a quantitative analysis of target materials or substances (e.g., protein, nucleic acid, etc.) using a nitrocellulose membrane, the protein that is used as a capture molecule (e.g., one that selectively binds to a target material of interest) is often printed onto a nitrocellulose membrane and drying the resulting nitrocellulose membrane. In this manner, the capture molecule is immobilized onto the nitrocellulose membrane without producing a covalent bond between the capture molecule and the nitrocellulose membrane surface (FIG. 1). Without being bound by any theory, such a non-covalent immobilization or attachment of capture molecule onto the surface of nitrocellulose membrane can be achieved by a variety of chemical and/or physical means, such as, but not limited to, ionic interaction, hydrogen bonding, hydrophobic interaction, van der Waals interaction, etc. Moreover, and again without being bound by any theory, in a non-covalently attachment, a combination of one or more such a chemical and/or physical interactions may be involved in immobilization of a capture molecule onto the surface of nitrocellulose membrane. It is believed the non-covalent attachment of captive material (or capture molecule) to the surface of nitrocellulose membrane is a thermodynamic phenomenon, with the dipole moment interactions and/or hydrophobic interactions being believed to be one of the major factors or elements of the phenomenon.

Nitrocellulose membranes are porous structured polymers that can function as a chromatography matrix having a substantially unidirectional flow of solutions. This substantially unidirectional flow allows nitrocellulose membrane to be used in a flow-through test kits in a variety of diagnostic assays. As with any flow-through test or diagnostic kit, if the target material passes through the fixed region containing the capture molecule without forming a capture molecule-target material complex, the presence of the target molecule in a sample cannot be accurately determined. Moreover, if the flow rate is different from one test to another, the test or diagnosis kit will not be reliable. Therefore, an accurate and reliable test or diagnostic kit needs to provide a sufficient time for a capture molecule-target material complex to form. Conventional method for producing a constant flow rate in nitrocellulose membrane is to adjust the pore size of the membrane.

Unfortunately, flow rate and pore size are not the only factors required for accuracy and reliability of a flow-through test or diagnostic kits. For example, even if the target material passes through the capture molecule bound to the surface of the membrane with a sufficient time to form a complex between the capture molecule and the target material, often the desired complex is not formed because the reaction sites required to form a capture molecule-target material complex may be obscured or inaccessible due to the improper orientation or the presence of multiple layers of capture molecule on the surface of the nitrocellulose membrane. These factors also result in a low reproducibility and reliability of the flow-through test or diagnostic kits that use nitrocellulose membranes.

Therefore, there is a continuing need for a highly reproducible and reliable nitrocellulose membrane-based test and/or diagnostic kits.

SUMMARY OF THE INVENTION

One aspect of the invention provides a highly reproducible and reliable test and/or diagnostic kit using a nitrocellulose membrane. The nitrocellulose membrane of the present invention includes a non-covalently bound organic nanostructure (i.e., organic nanostructured molecule). In some embodiments, the organic nanostructured molecule comprises a covalently attached (i.e., covalently bound) capture molecule or capture material that is capable of selectively binding to a target material or a target substance. Without being bound by any theory, it is believed that the use of organic nanostructured molecule allows a more efficient and favorable presentation of the capture molecule to the target material, thereby resulting in a more accurate and reliable test/diagnostic kit.

It is believed that use of organic nanostructured molecules of the invention results in reaction or binding sites that are more accessible and more structured (i.e., not clumped or in multiple layers) resulting in a significant reduction in steric hindrance for binding between the capture molecule and the target material. The same effect can be obtained when the capturing molecule is attached or printed to the organic nanostructure molecule after attaching the organic nanostructure to the membrane support. Use of organic nanostructure molecules to attach the capture molecule modifies the spatial environment of the capture molecule on the surface of the nitrocellulose membrane creating an environment where the target material and the capture molecule are allowed to more readily form a complex. The resulting nitrocellulose membrane provides a highly reproducible and highly reliable quantitative and qualitative analysis of target materials.

Another aspect of the invention provides a highly reproducible quantitative analysis method of a target material. The target material selectively binds to a capture molecule that is covalently attached to an organic nanostructure molecule of the invention. In turn, the organic nanostructure molecule is non-covalently attached to a nitrocellulose membrane, which is used as a support.

Yet another aspect of the invention provides a quantitative and/or qualitative assay kit. In some embodiments, the assay kit enables quantitative determination of a target material with high reproducibility.

In some embodiments, the organic nanostructure molecule comprises a plurality of branched regions and a linear region. The terminal end of the linear region comprises a functional group that can be used to covalently attach a capture molecule. Alternatively, the capture molecule can be attached to the terminal end of the linear region prior to non-covalently attaching the organic nanostructured molecule to the nitrocellulose membrane. In some embodiments, the organic nanostructured molecule comprises a plurality of (e.g., at least two, typically at least three, and most often three, nine or twenty-seven) branched region terminal end functional groups that are capable of forming a non-covalent attachment to the nitrocellulose membrane. The branched region terminal end functional group can be either positively charged or negatively charged.

Yet another aspect of the invention provides a quantitative and/or qualitative analysis method of a target material using the nitrocellulose membrane described herein.

Still another aspect of the invention provides a quantitative and/or qualitative assay kit that includes a nitrocellulose membrane (NCM) of the present invention.

The invention also provides an organic nanostructure molecule that is useful inter alia for quantitative and/or qualitative analysis of a target material. The organic nanostructured molecule of the invention includes a plurality of branched region terminal end functional groups and a linear region terminal functional group that can be used to covalently attach a capture molecule.

In some embodiments, use of the nitrocellulose membrane of the invention provides at least 10%, typically at least 25%, and often at least 50% improvement in selectivity and/or specificity compared to a conventional nitrocellulose based assay test, such as those with polyethylene glycol ("PEG") based linkers. Yet in other embodiments, use of the nitrocellulose membrane of the invention provides improved reproducibility of at least 100%, typically at least 200%, often at least 300%, more often at least 400%, and most often at least 500% as illustrated in FIG. 4.

BRIEF DESCRIPTION OF THE DRAWINGS

FIG. 2-1 is a schematic diagram showing attachment of a capture molecule on nitrocellulose membrane using an organic nanostructured molecule in accordance with one embodiment of the present invention.

FIG. 2-2 is a schematic diagram showing attachment of a capture molecule on nitrocellulose membrane using an organic nanostructured molecule in accordance with another embodiment of the present invention.

DETAILED DESCRIPTION OF THE INVENTION

Figure 1:
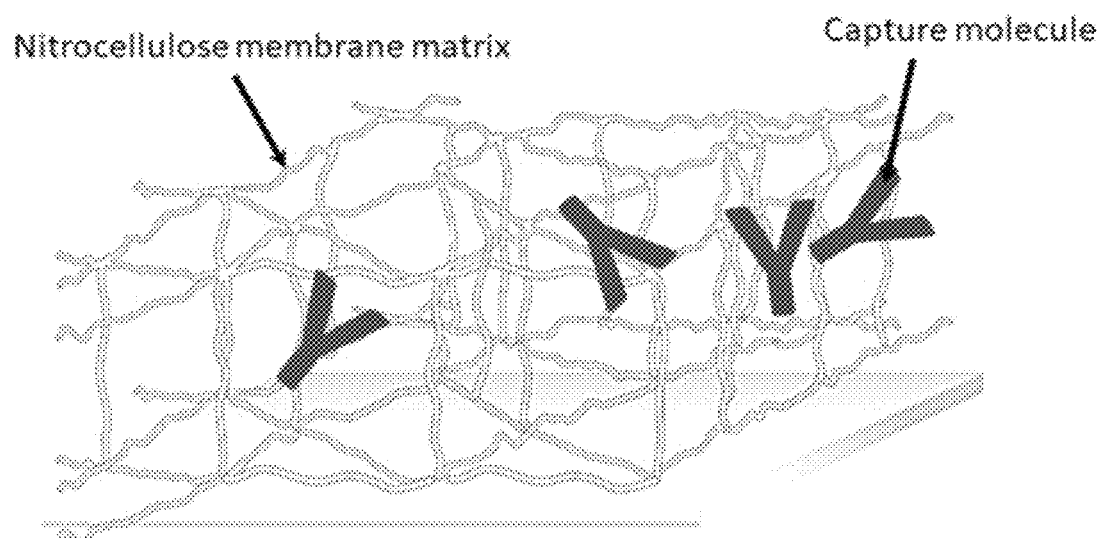
FIG. 1 is a schematic drawing in which the capturing material of the conventional method is immobilized on the surface of a nitrocellulose membrane (NCM).

The following discussion of the invention is presented merely for purposes of illustrating some aspects of the present invention and is not intended to limit the scope of the present invention. Although the description of the invention includes description of one or more embodiments and certain variations and modifications, other variations and modifications are within the scope of the invention, e.g., as may be within the skill and knowledge of those in the art, after understanding the present disclosure. It is intended that the scope of the present invention includes alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

The terminology used herein is for the purpose of describing particular application only, and is not intended to limit the invention. The singular forms "a," "an," and "the" include plural referents unless the context clearly dictates otherwise.

One particular aspect of the invention provides a nitrocellulose membrane (NCM) that is useful for quantitative and/or qualitative analysis of a target material. In one embodiment, the NCM comprises an organic nanostructure molecule that is non-covalently attached to the NCM. The organic nanostructured molecule of the invention includes a plurality of branched regions each of which can include a terminal end functional group that can be used to non-covalently attach to the NCM. The branched region terminal functional groups can be positively or negatively charged. The organic nanostructured molecule also includes a linear region that includes a functional group capable of covalently attaching or bonding to a capture molecule. It should be appreciated that the scope of the invention includes organic nanostructured molecule in which the capture molecule is already covalently attached to the organic nanostructured molecule.

The organic nanostructure molecule of the invention comprises a central atom; a branched region having a plurality of terminal end moieties; and a linear region having a terminal end functional group. The linear region terminal end functional group is used to covalently attach a capture molecule as described in detail herein. A plurality of branched region terminal end moieties (i.e., a plurality of branched region terminal end function groups) is used to non-covalently attach the organic nanostructured compound to a porous nitrocellulose membrane. Typically, nitrocellulose membrane used in the invention has a median pore diameter size of from about 0.05 µm to about 30 µm, typically from about 1 µm to about 30 µm, often about 5 µm to about 20 µm, and more often about 10 µm to about 15 µm. Unless context requires otherwise, as used herein the term "about" when referring to a numerical value means ±20%, typically ±10%, often ±5%, and most often ±1% of the numerical value. In some embodiments, the terminal end functional group of the linear region includes a covalently bound capture molecule.

While a wide variety of methods can be used to non-covalently attach organic nanostructured molecule to nitrocellulose membrane, one particular embodiment of the invention includes immobilizing an organic nanostructure molecule on a surface or the matrix of a porous nitrocellulose membrane by a plurality of non-covalent attachments. The organic nanostructure comprises: (i) a central atom; (ii) a branched region having a plurality of terminal end moieties that are non-covalently attached to the surface of said porous nitrocellulose membrane; and (iii) a linear region having a covalently bound capture molecule on a terminal end of said linear region, wherein said capture molecule is adapted to selectively bind to the target material when the target material is present in the sample. The organic nanostructured molecule can be attached to the nitrocellulose membrane by any of the known methods including, but not limited to, a printing process. The printing process includes, for example, use of a jet-print technology where a solution of organic nanostructured molecule is printed on a nitrocellulose membrane and allowing the printed solution to dry. This printing technology allows fixation of organic nanostructured molecule to the nitrocellulose membrane by a plurality of non-covalent bonding.

Figures 1, 2:
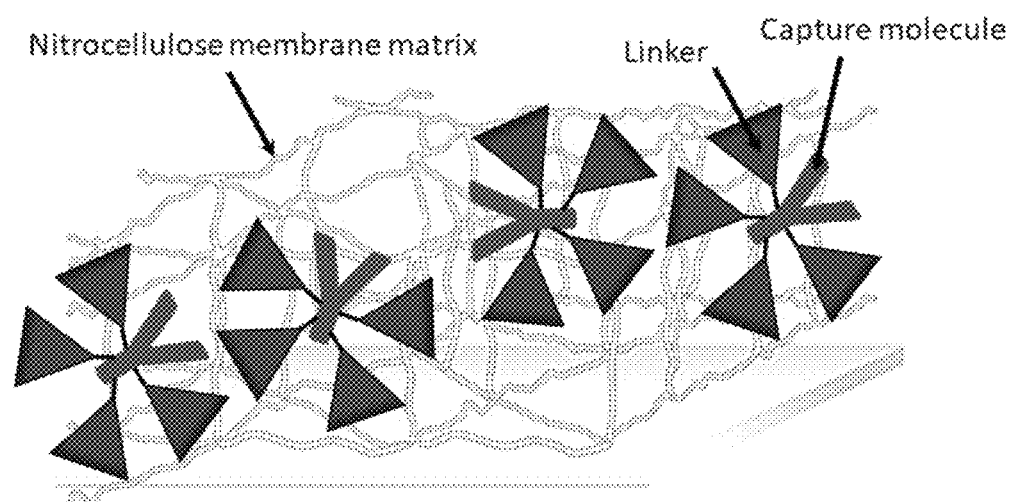
Figure 2:
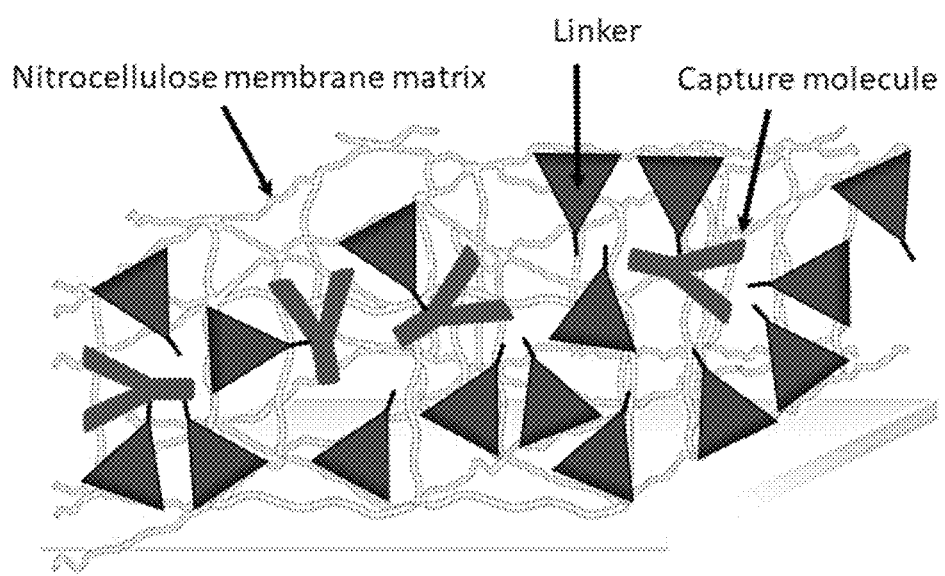

Alternatively, the organic nanostructured molecule is immobilized on the nitrocellulose membrane (e.g., via a printing process) and reacting a capture molecule with the functional group of the terminal end of the linear region of the organic nanostructured molecule under conditions sufficient to produce a linear region of the organic nanostructure that is covalently attached to the capture molecule. In some embodiments, the capture molecule is printed onto the same area of the nitrocellulose membrane that is non-covalently attached to the organic nanostructured molecule and the resulting area is allow to react and dry prior to using the nitrocellulose membrane in a quantitative and/or qualitative assay. Without being bound by any theory, it is believed that use of the organic nanostructured molecule in attaching the capture molecule to the nitrocellulose membrane controls the distance between the capture molecule-target material complex as illustrated in FIG. 2, thereby significantly reducing the steric hindrance.

An assay method involves using the nitrocellulose membrane described herein (e.g., as a flow-through assay kit or a lateral flow assay kit), and contacting a sample or a specimen to the nitrocellulose membrane to determine the presence of and/or the quantity of the target material within the sample or the specimen. As used herein, the terms "sample" and "specimen" are used interchangeably herein and refers to a material that is being analyzed. Such a sample can be a bodily fluid sample (e.g., blood, saliva, stool, urine, mucous, etc.), biological sample (e.g., cell, DNA, protein, bacteria, virus, etc.), a chemical sample, a food sample, an environmental sample (e.g., soil, atmosphere, etc.), as well as any other sample that can be analyzed. Typically, the assay is conducted using a lateral flow or a flow-through process to bind the target material (if present) to the capture molecule.

The assay process can also include adding a detecting material, e.g., signal tracer such as a fluorophore, an enzyme (horseradish peroxidase, alkaline phosphatase, etc.), a colloidal gold, etc., to the nitrocellulose membrane to determine the presence of or the quantity of capture molecule-target material complex. Analysis can include reacting the capture molecule-target material complex with a detecting material similar to those used in ELISA.

The detecting material can include a moiety that is adapted to generating colorimetric, chemiluminescence, or chemifluorescence signals. In this manner, the signal that is generated (e.g., color, luminescence, or fluorescence signals, respectively), can be analyzed using an optical sensor. The signal can also be analyzed for its signal level to allow quantification of the capture molecule-target material complex that is formed on the nitrocellulose membrane. As an example, if the detecting material includes a fluorescent signal generating moiety, the nitrocellulose membrane is irradiated with the light of excitation wavelength and the fluorescence intensity can be quantified to determine the quantity of target material present in the sample. When the detecting material includes colloidal gold, the degree of color development is obtained in the optical system using the parameter of colorimetry of the optical device to quantify the amount of target material present in the sample.

Signals obtained, e.g., using an optical equipment, can be quantified or semi-quantified using a graph between the target material concentration and the signal value, a trend line, a standard equation, and a coefficient of determination.

In some embodiments, methods of the invention can be used to reliably analyze a wide variety of target materials such as a cell, a DNA, an RNA, a PNA, an aptamer, a ligand, an exosome, a lipid. Unless the context requires otherwise, the term "analyze" or "analysis" means qualitative and/or quantitative analysis.

The invention also provides an analysis method of the target material using the nitrocellulose membrane, comprising the following steps: (i) adding a sample to a nitrocellulose membrane of the invention under conditions sufficient to form a capture molecule-target material complex, when the target material is present in the sample; (ii) contacting the resulting nitrocellulose complex with a detecting material to form a detecting complex when the capture molecule-target material complex is present on the nitrocellulose membrane; and (iii) analyzing the signal generated from the detecting complex to determine the presence of and/or the quantity of the target material present in the sample.

The sample is typically presented as a solution. Exemplary samples that can be analyzed using the methods of the invention include, but are not limited to, blood, serum, plasma, saliva, urine, a biological sample such as fecal, sputum or tissue, and environmental samples such as a water sample, a soil sample, an air sample, and a food sample such as meat, fish, vegetable, beverage, dried food, processed food, etc.

The target material of can be any substance that requires analysis such as an antigen, an antibody, a protein, a peptide, a DNA, an RNA, a PNA, an aptamer, a ligand, a toxic compound, lipids, hormones, minerals, bacteria, viruses, macro-vesicles or micro-vesicles, exosomes, cells, etc.

The capture molecule can be any molecule that can selectively binds to the target material. Exemplary capture molecules include, but are not limited to, an antigen, an antibody, DNA, RNA, PNA, aptamer, a ligand, a lipid, a hormone, etc.

The detection material can also include a signal body or a detection moiety such as, but not limited to, a fluorophore, a magnetic particle, an enzyme, a nanoparticle, a nanofiber, etc.

In the present invention, depending on the molecular weight or structure of the organic nanostructured molecule, the distance and density between capture molecules present on the nitrocellulose membrane surface can be controlled. In one particular embodiment, the distance between the linear region terminal end functional groups (or the capture molecule attached thereto) of the organic nanostructured molecule can be controlled in the range of from about 0.5 nm to about 10 nm. Alternatively, the density of capture molecule on the nitrocellulose membrane can be adjusted in the range of from about 0.01 to about 0.1 capture molecules per nm$^2$.

The analysis method using the nitrocellulose membrane of the invention comprising a non-covalently attached organic nanostructured molecule having a covalently attached capture molecule can be used in the form of an assay kit and can also be applied to a diagnosis method. In one particular embodiment, the assay kit of the invention is manufactured in a lateral flow type or a flow-through type assay kit. However, it should be appreciated that the scope of the invention is not limited to these particular assay kits.

The present invention also provides an organic nanostructured molecule that can be used to covalently attach a capture molecule to a nitrocellulose membrane. The organic nanostructured molecule includes a linear region having a terminal end functional group that is used to covalently attach a capture molecule. The organic nanostructured molecule also includes a plurality of branched regions. The plurality of branched regions include a terminal functional group that can be used to non-covalently attach the organic nanostructure molecule to the nitrocellulose membrane.

The terminal end functional group of linear region that can be used to covalently attach a capture molecule can be, for example, a hydroxyl group, a formyl group, a carbonyl group, a carboxy group, an ether group, an ester group, a nitro group, an amino group, a sulfonic acid group, a phenyl group, an alkyl group, a phosphine group, an N-hydroxysuccinimide-ester group, an aldehyde group, an epoxide, an azlactone, a carbonyl diimidazole, a maleimide, an iodoacetyl, a pyridyl disulfide, a pyridyl disulfide, a hydrazide hydrate, or EDC (1-Ethyl-3-(3-dimethylaminopropyl) carbodiimide) HCl). Typical terminal end functional group of the linear region is selected from the group consisting of an aldehyde group and an epoxide group. However, it should be appreciated that the scope of the invention is not limited to the above terminal end functional groups of the linear region.

In some embodiments, the linear region of the organic nanostructured molecule includes at least one ether group. The presence of ether group improves the hydrophilic property of the organic nanostructured molecule.

Yet in other embodiments, each of the terminal end functional groups of the branched region of the organic nanostructured molecule is selected from the group consisting of an amino group, a sulfonic acid group, a phenyl group, an alkyl group, a phosphine group, an aldehyde group, hydroxyl group, formyl group, carbonyl group, carboxy group, ether group, ester group, nitro group, and an epoxide group. However, it should be appreciated that the terminal end functional groups of the branched region is not limited these functional groups. In general, any suitable functional groups that allows non-covalently attachment of the of the organic nanostructured molecule to the nitrocellulose membrane can be used.

Still in other embodiments, the branched regions of the organic nanostructured molecule include at least two, often at least three, and typically three, nine or twenty-seven, terminal end functional groups adapted to non-covalently attach the organic nanostructure molecule to the nitrocellulose membrane.

In some embodiments, the organic nanostructured molecule comprises a triazole moiety on its linear region. Surprisingly and unexpectedly, the present inventors have found that the presence of a triazole moiety on the linear region of the organic nanostructured molecule provides a highly reproducible and reliable nitrocellulose membrane assay kit. Furthermore, the presence of a triazole moiety on the linear region also allows a relatively rigid structure and ease of synthesis compared to other linear region moieties. In one particular embodiment, the organic nanostructured molecule is of the formula:

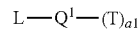

Formula A where

L is a linear region moiety of the organic nanostructured molecule comprising a triazole moiety, wherein L further comprises:
 (i) a linear region terminal functional group adapted for covalently attaching a capture molecule that is adapted to selectively bind to a target molecule, or
 (2) a covalently attached capture molecule that is adapted to selectively bind to a target molecule;

$Q^1$ is a central atom of said organic nanostructured molecule having an oxidation state of at least 3;

$a^1$ is an integer from 2 to the oxidation state of $Q^1-1$; and each T is independently a branched terminal region moiety of said organic nanostructured molecule comprising a branched terminal region functional group that is adapted to non-covalently attaching said organic nanostructured molecule to said porous nitrocellulose membrane;

and wherein said organic nanostructured molecule is non-covalently attached to said porous nitrocellulose membrane by a plurality of said branched terminal region functional groups.

In some embodiments, L comprises a trialzolyl moiety. Still in other embodiments, L comprises 1,2,3-triazolyl moiety. Yet in other embodiments, L comprises 1,4-substituted 1,2,3-triazolyl moiety.

In one particular embodiment, L comprises a moiety of the formula:

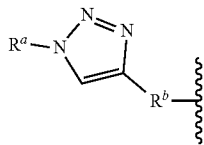

where $R^a$ is as defined herein and $R^b$ is a linker attached to $Q^1$. In some embodiments, $R^b$ is a linker having from about 2 to about 10, typically from about 2 to about 8, often about from 2 to about 6 and more often from 2 to 4 atom chain. In one particular embodiment, $R^b$ is a moiety of the formula —(CH$_2$)$_2$—C(=O)—NR$^c$—, where $R^c$ is hydrogen, C$_{1-4}$ alkyl or a nitrogen protecting group. The term "alkyl" refers to a saturated linear monovalent hydrocarbon moiety of one to twelve, typically one to six, carbon atoms or a saturated branched monovalent hydrocarbon moiety of three to twelve, typically three to six, carbon atoms. Exemplary alkyl group include, but are not limited to, methyl, ethyl, n-propyl, 2-propyl, tert-butyl, pentyl, and the like.

It should be appreciated that when $a^1$ is an integer less than the oxidation state of $Q^1$–1, then $Q^1$ can be attached to a hydrogen or an alkyl group, e.g., when $Q^1$ is C and $a^1$ is 2, then the compound of Formula A can be represented as: L-CH(T)$_2$ or L-CR$^1$(T)$_2$, where $R^1$ is alkyl such as methyl, ethyl, etc.

Yet in another embodiment, the organic nanostructured molecule is of the formula:

IA

L—Q$^1$—{[R$^2$—Q$^2$]$_a$—{(R$^3$—Q$^3$)$_b$—[(R$^4$—Q$^4$)$_c$—(R$^5$—Y)$_x$]$_y$}$_z$}$_n$ where
each of a, b, and c is independently 0 or 1;
x is 1 when c is 0 or when c is 1, x is an integer from 1 to the oxidation state of Q$^4$–1;
y is 1 when b is 0 or when b is 1, y is an integer from 1 to the oxidation state of Q$^3$–1;
z is 1 when a is 0 or when a is 1, z is an integer from 1 to the oxidation state of Q$^2$–1;
n is an integer from 1 to the oxidation state of Q$^1$–1;
L and Q$^1$ are as defined herein;
each of Q$^2$, Q$^3$ and Q$^4$ is independently a branch atom having the oxidation state of at least 3;
each of R$^2$, R$^3$, R$^4$, and R$^5$ is independently a linker; and
Y is said branched terminal region functional group,
provided the product of n, x, y, and z is at least 3. The linkers R$^2$, R$^3$, R$^4$, and R$^5$ can be alkylene (e.g., methylene, ethylene, propylene, etc.) optionally having a heteroatom such as O, S, or NR (where R can be H or C$_1$-C$_6$ alkyl). The term "alkylene" refers to a saturated linear saturated divalent hydrocarbon moiety of one to twelve, preferably one to six, carbon atoms or a branched saturated divalent hydrocarbon moiety of three to twelve, preferably three to six, carbon atoms. Exemplary alkylene groups include, but are not limited to, methylene, ethylene, propylene, butylene, pentylene, and the like. In some embodiments, each of R$^2$, R$^3$, R$^4$, and R$^5$ is independently selected from the group consisting of —CH$_2$—; —CH$_2$—O—; —CH$_2$—CH$_2$—; —CH$_2$—CH$_2$—O—; —O—CH$_2$—CH$_2$—; —CH$_2$—CH$_2$—CH$_2$—O—; —O—CH$_2$—CH$_2$—CH$_2$—; and the like.

Still in another embodiment, the organic nanostructured molecule is of the formula:

IB

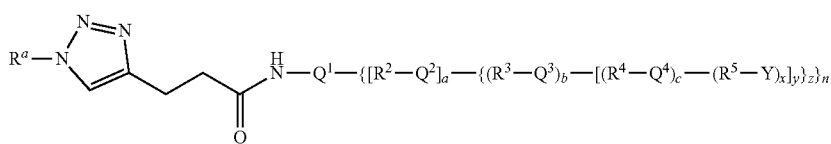

where
Q$^1$, Q$^2$, Q$^3$, Q$^4$, R$^2$, R$^3$, R$^4$, R$^5$, Y, a, b, c, x, y, z, and n are as defined herein;
R$^a$ is selected from the group consisting of:

(Formula L1)

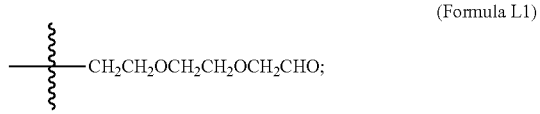

(Formula L2)

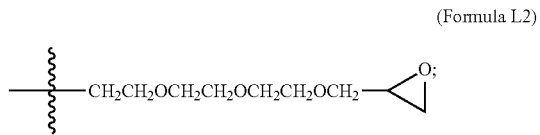

(Formula L3)

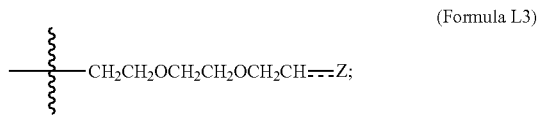

(Formula L4)

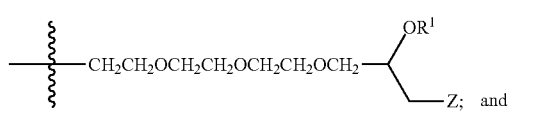

and a combination thereof,
where
a dotted line represents optional double bond;
Z is the capture molecule that is adapted to selectively bind to a target molecule,
and wherein said Z is covalently attached using the aldehyde functional group of compound of Formula L1 or the epoxide functional group of compound of Formula L2.

Yet in another embodiment, the organic nanostructured molecule is of the formula:

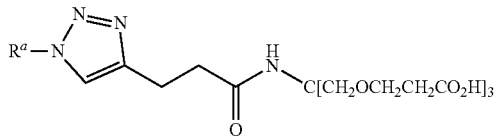

wherein $R^a$ is as defined herein.

Some exemplary organic nanostructured molecules are of the formula:

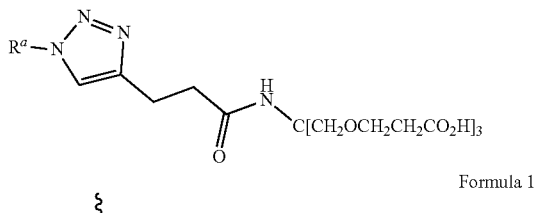

Formula 1

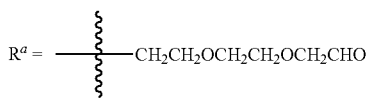

Formula 2

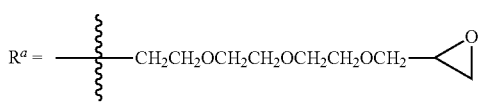

In general, unless otherwise defined, terms used herein are well known to those skilled in the art of organic chemistry and biochemistry. Some of the specific terms used herein are defined as follows.

The term "sample" refers to a liquid or a solution sample including, but not limited to, an emulsion, a dispersion, a homogeneous solution, and a suspension.

The term "biological fluid" refers to all clinical samples. Exemplary biological fluids include, but are not limited to, blood, plasma, serum, urine, mucous, spinal fluid, saliva, and any other biological fluid that is excreted, secreted, or transferred internally from the organism.

Unless the context requires otherwise, the terms "capturing molecule", "capture molecule", "capturing material", and "capture material" are used interchangeably herein and refer to a substance capable of directly or indirectly binding to a target material. Exemplary capture molecules include, but are not limited to, nucleic acids (e.g., DNA, RNA, PNA and the corresponding oligonucleotides), a receptor, a ligand, an enzyme, a protein, aptamer, as well as any other substrate that can selectively bind to a target material. In one specific example, the capture molecule is an antibody having a strong binding ability to a desired antigen.

The terms "detecting molecule", "detecting material", "detecting substance", and "detecting moiety" are used interchangeably herein and refer to a substance that allows detection or observation of a complex that is formed between the capture molecule and the target material. The detecting molecule can be part of the capture molecule and/or the target material. Thus, the detecting molecule need not necessary be a separate molecule.

The capture molecule can be any substance that can specifically recognize the target material with different recognizing sites targeted by the capture molecule. For example, the capture molecule can be (i) an antibody including a polyclonal antibody purified from an antiserum obtained by immunizing a mammal with a target substance, (ii) an antibody-producing cell extracted from a mammal immunized with the target substance, and (iii) a monoclonal antibody produced from a hybridoma obtained by fusion with myeloma cells can be used. The polyclonal antibody to the target substance can be obtained by purification method known to one skilled in the art, such as (i) salting-out an antiserum, (ii) ion exchange chromatography, (iii) affinity chromatography, etc. The monoclonal antibody to the target material can be obtained by one skilled in the art such as: immunizing a suitable animal such as a mouse with a target substance, fusing the splenocyte with myeloma cells, and using method such as ELISA, selecting a clone producing an antibody that specifically binds to target material, and then using ascites obtained by inoculating a suitable supernatant or hybridoma into an appropriate animal. Antibodies against the target material thus obtained can be used to as capture molecules by immobilizing the antibody on a support such nitrocellulose membrane as described herein.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies can be produced, for example, according to the methodology of Kohler and Milstein (Nature, 1975, 256, 495-497). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

Antibodies may also be used as a detection material to recognize a target material complexed with a capture molecule by labeling a signal moiety such as an enzyme, a fluorescent substance, or a colloidal gold on the antibody. As an antibody having a signal moiety-labeled detection material, typically a monoclonal antibody is used in order to obtain a high selectivity for a target substance. However, when the capture molecule is a monoclonal antibody, the polyclonal antibody can be used as a detection material.

The term "incubation" in the present invention means that the reaction between the antigen-antibody or the complementary DNA or RNA are preserved at a constant temperature (e.g., within ±5° C., typically within ±3° C. and often within ±1° C.). An antigen-antibody reaction is a selective binding of an antibody to an antigen having a complementary structure. As used herein, a complementary DNA or RNA reaction is a reaction in which DNA or RNA of each strand having 100% complementary base sequence for hybridization. Thus, the composition and method of the invention can be used to distinguish a single nucleotide polymorphism ("SNP")\.

The term "washing" is used in a widely acceptable manner. Typically, the term "washing" means washing or removing the remaining material using a solvent or a solution without reacting with a capture molecule or the target material (e.g., antibody or a nucleic acid hybridization) in the incubation process. There is no particular limitation as long as it does not affect the formation of capture molecule-target material complex (e.g., antigen-antibody or nucleic acid hybridization). A surfactant may be added to enhance the cleaning or washing effect. In addition, the washing or cleaning method is not particularly limited as long as it is effective for the overall complex formation process. Washing or cleaning is optional step that may be performed to increase the sensitivity of the analysis by removing a potentially signal interfering substance.

In the present invention, the reaction temperature in the step of incubation and signal body signal generation is not particularly limited. However, in order to prevent the loss of enzyme signal activity or reaction solution from freezing or evaporating, the binding of capture molecule to a target material is conducted at a temperature range of from about 4° C. to about 40° C. When a quick signal termination is desired in an enzyme-ligand complexation, the temperature range of complex formation typically ranges from about 15° C. to about 40° C.

During an incubation process of forming a complex between a capture molecule and a target molecule, a longer incubation time generally leads to a higher amount of capture molecule-target material complex formation. However, the binding (i.e., complex formation) reaction can become saturated after a certain period of time. In order to provide a quick analysis, it is desirable to reduce the complex formation (i.e., incubation) time. The greater the amount of capturing molecule is loaded (i.e., non-covalently immobilized) on the NCM support, the greater the sensitivity, and the reaction or incubation time can be shortened as more target material can be complexed to the capture molecule. On the other hand, a portion where the target material makes steric hindrance by blocking the reaction (i.e., complex formation) site, the efficiency is lowered; therefore, it is necessary to optimize the amount of capture molecule loaded (i.e., immobilized) on to the nitrocellulose membrane. As used herein, the term "immobilized" when referring to attachment of organic nanostructured molecule to a nitrocellulose membrane refers to having substantially all (typically ≥90%, often ≥95% and most often ≥99%) of the organic nanostructured molecule in a dried nitrocellulose membrane remain attached to the nitrocellulose membrane during an assay process.

Since the capture molecule is immobilized on the surface of the nitrocellulose membrane via an organic nanostructured molecule, the distance between each capture molecules can relatively be controlled by the organic nanostructured molecule. This eliminates or significantly reduces the problem of unsatisfactory reproducibility in the quantitative analysis due to steric hindrance.

The term "fluorescence", "chemiluminescence", "chemifluorescence" and "colorimetric" are well recognized to one skilled in the art. Typically, these terms refer to the fact that a color or light (fluorescence, luminescence) is emitted or can be detected using any of the analytical methods known to one skilled in the art.

During an analysis step of methods disclosed herein, the signal can be measured or determined semi-quantitatively or qualitatively using the naked eye. Typically, however, the signal is measured by an instrument (e.g., a colorimetric instrument, UV/Vis spectrometer, etc.) to quantitatively or qualitatively analyze the signal. As well known to one skilled in the art, "chemiluminescence", "chemical fluorescence", and "fluorescence" are typically measure the intensity of fluorescence or chemiluminescence emitted by image sensor of an optical device system. Such a signal can be quantitatively or qualitatively analyzed.

Unless the context requires otherwise, the terms "detection" and "analysis" refer to steps to confirm the presence of a target material. The terms include qualitative determination for confirming the presence or absence of the target material as well as a quantitative or semi-quantitative determination of target substance concentration.

Typically, the sample is a fluid or a solution having a fluidity in order to facilitate the selective or specific binding between the target material (if present in the sample) and the capture molecule that is immobilized on the NCM support. However, it should be appreciated that the sample is not limited to a fluid. For example, if it the sample is a solid, it may be dissolved or dispersed in a solution using a suitable solvent.

With regards to the amount of sample required for the measurement (i.e., assaying), there is no particular requirement for the amount of sample required as long as the amount of sample is sufficient enough to allow detection/quantization of the target material, if present in the sample, by the capture molecule affixed on the NCM support. The sample can be diluted prior to assaying. However, diluting the sample will lower the concentration of the target material. Therefore, there is a possibility that detection or quantification of the target material may become difficult due to decreased concentration of the target material in the sample. In such a case, the incubation time may be increased to allow a sufficient time for formation of the capture molecule-target material complex, if the target material is present in the sample. Alternatively, the amount of capture molecule can be increased in order to compensate for the reduced concentration of the target material. Typical amount of the sample used in an analytical method of the invention ranges from about 10 µL it to about 200 µL. However, it should be appreciated that the amount of sample used in analysis is not limited to these ranges. In fact, any amount of sample that is sufficient to allow formation of a complex between the capture molecule and the target material can be used in methods of the invention.

The capture molecule that is immobilized on the NCM support is covalently attached to the organic nanostructured molecule's linear region terminal end functional group. Suitable linear region terminal end functional groups of the organic nanostructured molecule include, but are not limited to, a hydroxyl, a formyl, a carbonyl, a carboxyl, an ether group, an ester group, a nitro group, an amino group, a sulfonic acid group, a phenyl group, an alkyl group, a phosphine group, N-hydroxysuccinimide-ester, aldehyde, epoxide, azlactone, carbonyl diimidazole, maleimide, iodoacetyl, pyridyl disulfide, hydrazide, and EDC (1-Ethyl-3-(3-dimethylaminopropyl) carbodiimide) HCl).

In some embodiments, in order to avoid or to significantly reduce interaction between the desired target material and non-capture molecule portion of the nitrocellulose membrane, thereby generating a false positive signal, one can block or quench the non-capture molecule portion of the nitrocellulose membrane. For example, when the capture molecule is a protein, treating the nitrocellulose membrane with a solution containing casein, bovine albumin, or gelatin, significantly reduces or prevents non-selective interaction between the non-capture molecule portion of the nitrocellulose membrane and the target material.

Methods of the invention can be used to detect/analyze any target material desired. Exemplary target materials that can be detected/analyzed by nitrocellulose membranes and methods of the invention include, but are not limited to, biomaterials (such as antigens, antibodies, proteins, lipids, peptides, DNA, and RNA), toxic compounds, minerals, bacteria, viruses, macro and micro vesicles, exosome and cells, and non-biomaterials such as drugs, pigments, heavy metals.

Methods of the invention can also include capturing a target material with two antibodies (e.g., one as a capture molecule and the other as a detection material). Such a method is similar to an enzyme-linked immunosorbent assay ("ELISA") but offers a substantially higher reliability and reproducibility. Moreover, methods of the invention is significantly more accurate and requires a significantly less amount of the target material for detection/analysis. Such methods are particularly useful for target materials having a molecular weight of a peptide containing 12 to 15 amino acids.

When the target material is an inorganic substance such as a vitamin or a low molecular weight substance such as glucose, antibody as a capture molecule is not suitable. In such cases, mutual competition between materials similar to the target material and one particular signal tracer can be used.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

In this example, a capture molecule that is adapted to detect an acute myocardial infarction biomarker (i.e., cardiac troponin I(cTnI)) was used to determine the appropriate amount of the organic nanostructured molecule required for a highly reproducible quantitative analysis.

Aqueous solutions of potassium salt of the organic nanostructured molecule (MW 762.93, $C_{27}H_{41}K_3N_4O_{14}$) were prepared at a molar ratio of 0.4, 1.0, 4.1, and 5.1 relative to the number of moles of the capturing molecule, antibody specific for cTnI. The prepared organic nanostructure molecule solutions were dispensed onto a nitrocellulose membrane (CNPC, Advanced Microdevices, India) at a rate of 0.35 µL/cm to form a line, and dried in a dryer at 40° C. and a relative humidity of 10% for about 10 minutes. Thereafter, four types of nitrocellulose membranes having different amounts of organic nanostructured molecules were prepared by a similar process with drying in a dryer at 60° C. and a relative humidity of 10% or less for 24 hours. In order to compare the effect of the amount of organic nanostructured molecule, a nitrocellulose membrane supplied with no organic nanostructured molecule and water only was prepared as a control. The cTnI-specific capture antibody (0.027 mM, 0.35 µL/cm dispensing rate) was dispensed at the same position to regenerate the line, and dried in a dryer at 40° C. and 10% relative humidity for about 10 minutes, then it was dried in a dryer at 60° C. and a relative humidity of 10% or less for 24 hours.

Figure 3:
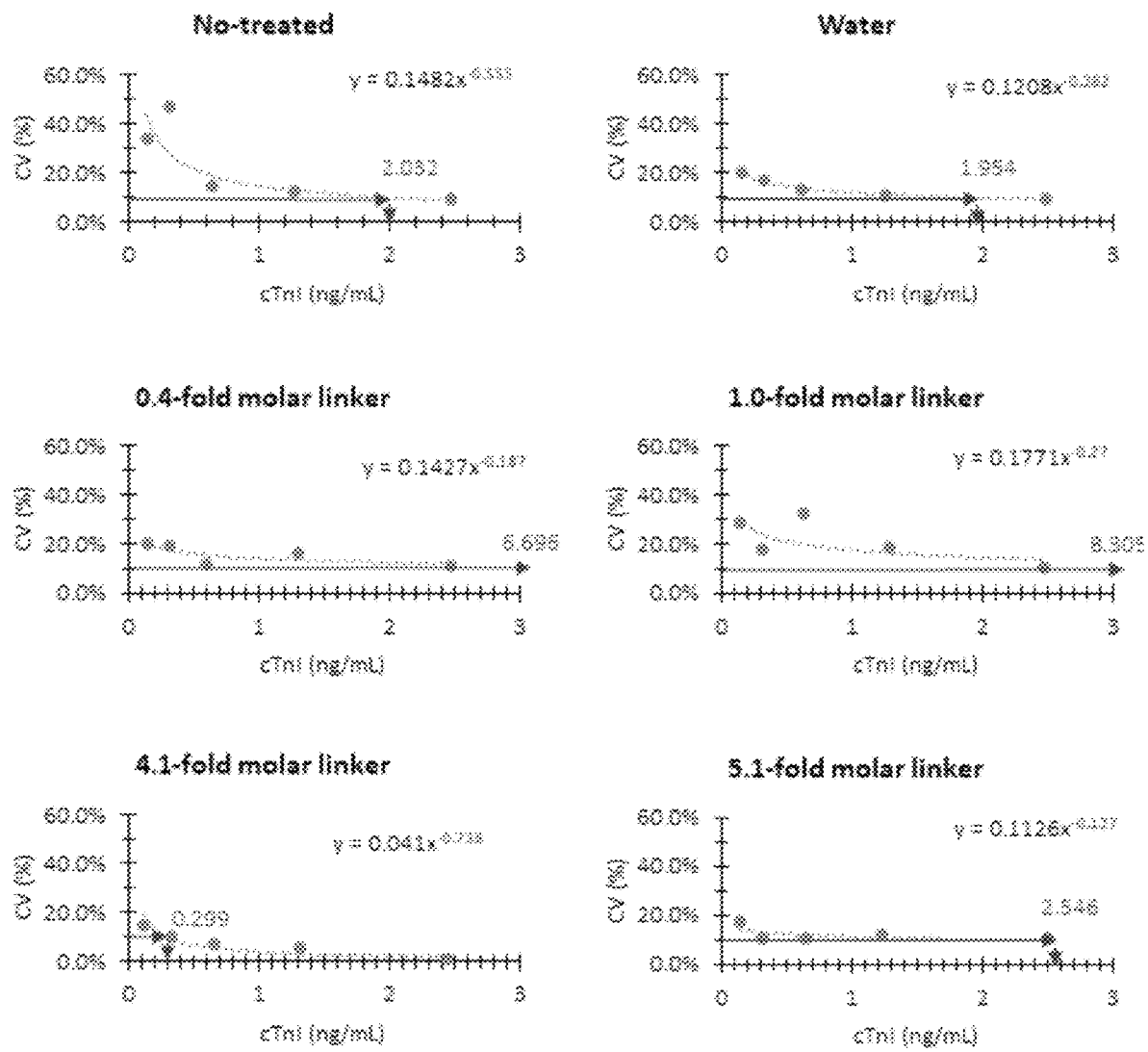
FIG. 3 is the graph showing the results of the reproducibility of the molar ratio between the capturing material from example 1 and the organic nanostructure with a concentration vs. CV (%) graph, a trend line and a standard equation, and concentration of CV 10%.

A lateral flow type kit was prepared using these membranes. Various concentrations of cTnI antigen (8T62, HyTest, Finland) diluted with human serum (Sigma-Aldrich, Louis, Mo.) (FSD™ 647, maximum excitation at 650 nm) was placed on the assay kit, followed by immunoblot binding with 100 µL of each test group and each control group. A 665 nm maximum emission moiety (BioActs, Korea) was sandwiched with a polymerized cTnI specific binding detection antibody (4T21 clone 19C7, HyTest, Finland). The fluorescence signal was detected using excitation light of a laser diode (650 nm) and a photodiode equipped with an optical filter with wavelength cut-off below 660 nm. Emitted 665 nm fluorescence was measured using a light-sensitive fluorescent reader. The measured fluorescence signal values were obtained by integrating the areas of the control line area and the test line area, and converting the test line area integration value into the T/C ratio divided by the control line area integration value. A standard curve was plotted for the concentration of target substance (cTnI) (FIG. 3).

Emissions of each sample were measured 16 times and converted using a standard equation obtained through the standard curve, and the CV (%) graph was obtained using the coefficient of variation (CV) calculated with the mean value and the standard deviation of the converted concentrations. (FIG. 3).

Concentration values at 10% CV of each supply amount of the organic nanostructures were compared using the equations obtained from the trend line in the form of a power line in CV graph against the sample concentration.

The concentration of 2.03 ng/mL at 10% CV was obtained from the control nitrocellulose membrane having immobilized capture molecule in the absence of an organic nanostructured molecule, and the concentration of 1.95 ng/mL at 10% CV was obtained from the control nitrocellulose membrane with immobilized capture molecule in the absence of an organic nanostructured molecule after the water treatment.

In the test group including organic nanostructured molecules of 0.4, 1.0, 4.1, and 5.1 times the relative number of moles of capture molecule, the concentrations at CV 10% were 6.70 ng/mL, 8.30 ng/mL, 0.40 ng/mL, and 2.55 ng/mL, respectively. Of the four different concentrations, the kits immobilized on a nitrocellulose membrane with treatment of 4.1 times the number of moles of organic nanostructured molecule compared to the capture molecule gave the best reproducible results (FIG. 3). In this lateral flow and rapid type inspection platform, the organic nanostructured molecule treated with 4.1 times the relative molar number of the capture molecule showed the CV 10% performance of about 5 times lower than that of the immobilized quantitative analysis indicating that the standard capacity has improved in terms of reproducibility.

Comparative Example 1

In this comparative example, the effects of nitrocellulose membranes from different manufacturers were examined. Briefly, lateral flow kits were prepared using 4.1 times molar excess of organic nanostructured molecule compared to the capture molecule and assayed for acute myocardial infarction markers in human serum. The detection of cTnI target substance as a biomarker was performed at 10% CV to compare the quantitative improvement effect. Nitrocellulose membranes from three different manufacturers (HF-135 from Millipore, Immuno-pore RP from GE healthcare, and CNPC from Advanced Microdevices) were immobilized with the capture molecule using an organic nanostructured molecule. For a control, a membrane was also immobilized with the capture molecule without the use of any organic nanostructured molecule.

Different concentrations ((0, 0.15, 0.3, 0.6, 1.25, and 2.5 ng/mL) of cTnI antigen (8T62, HyTest, Finland) in human serum (Sigma-Aldrich, Louis, Mo.) were prepared. A 100 samples were placed onto each test and control kit and sandwiched with cTnI specific binding detection antibody (4T21 clone 19C7, HyTest, Finland) polymerized with fluorescent (FSD$^{TM}$ 647, 650 nm maximum excitation, 665 nm maximum emission, BioActs, Korea). The fluorescence signal was detected by excitation light with a laser diode (650 nm) and a reader that detects 665 nm emission fluorescence using photodiode equipped with an optical filter that cuts off wavelengths below 660 nm was used.

The tests were repeated eight times each. Standard curve for the concentration of target material (cTnI) was obtained by integrating the area of the control and test line area and converting the test line area integration value into the T/C ratio. Using the standard equation obtained from the standard curve the average value and standard deviation were determined. These values were then used to calculate CV (%) and the CV graph of concentration was plotted. See FIG. 4. A trend line in the CV graph of the sample concentration was made in the form of exponentiation, and the concentration at CV 10% was calculated. Quantitative improvement effect was determined for nitrocellulose membrane from each manufacturer.

For control nitrocellulose membranes in which the capture molecule was immobilized without using an organic nanostructured molecule, CV 10% concentration of HF-135, Immuno-pore RP, and concentration of CNPC were 2.81 ng/mL, 5.94 ng/mL, and 1.73 ng/mL, respectively. See FIG. 4. For the test group membrane immobilized with the organic nanostructured molecule, the CV 10% concentration of HF-135, Immuno-pore RP, and CNPC were 0.96 ng/mL, 0.73 ng/mL, and 0.24 ng/mL, respectively. See FIG. 4.

Figure 4:
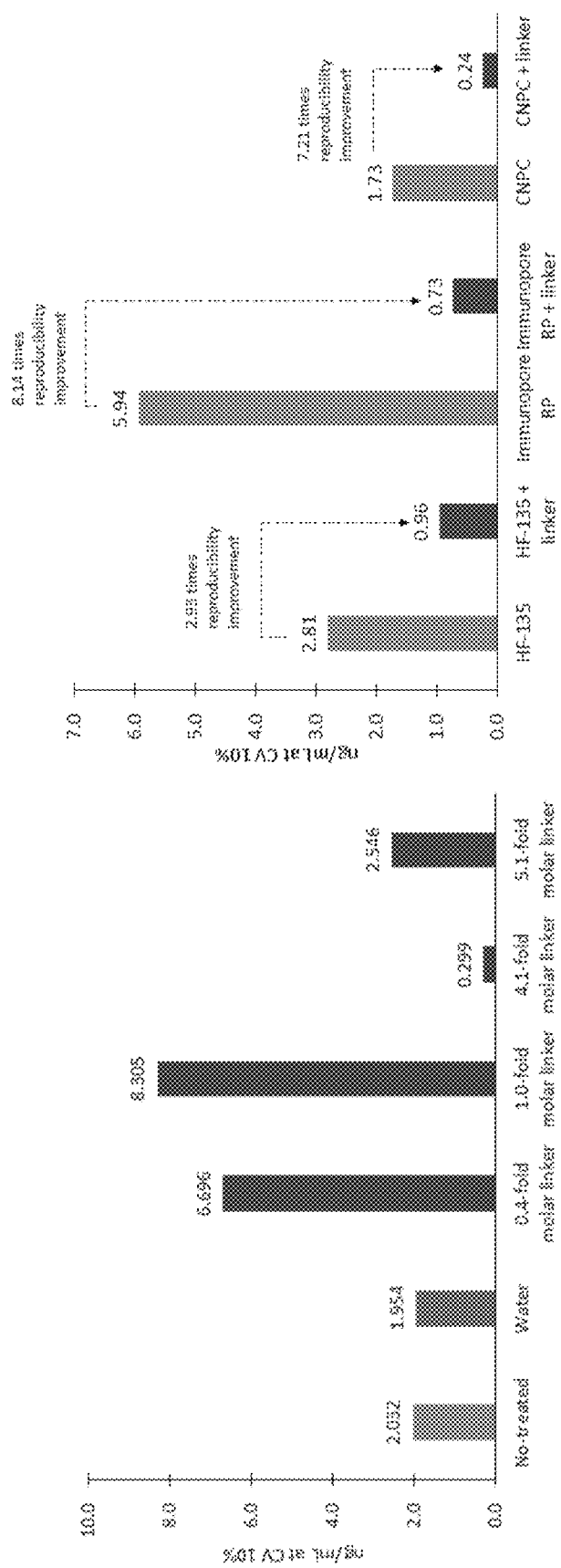
FIG. 4 is a graph showing the reproducibility results when the organic nanostructure was applied to each manufacturer's nitrocellulose membrane according to comparative example 1 at a CV of 10% and a reproducibility enhancement magnification.

As shown in FIG. 4, using an organic nanostructured molecule to immobilize a capture molecule led to an improved reproducibility of quantitative analysis ranging from 2.93 to 8.14 times compared to the control nitrocellulose membranes. See FIG. 4.

Example 2

This example demonstrates improvement in reproducibility of quantitative assay for a target material using a nitrocellulose membrane of the present invention.

In this example, a test assay kit was made by first covalently attaching a capture molecule to the organic nanostructured molecule using a linear region terminal end functional group of the organic nanostructured molecule. The linear region terminal end functional group of the organic nanostructured molecule used in covalently attaching the capture molecule was an aldehyde or an epoxide functional group. The organic nanostructured molecule was then non-covalently immobilized on to the nitrocellulose membrane using the procedure of Example 1. Assay tests were performed similar to that described in Examples above to determine improvement in quantitative assay reproducibility.

An organic nanostructured molecule having an aldehyde linear region terminal end function group was covalently bonded with a capture molecule. Briefly, the amount of organic nanostructured molecule used was 4.1 times the amount of capture molecule. Similarly, an organic nanostructured molecule having an epoxide linear region terminal end function group was covalently bonded with a capture molecule. Test nitrocellulose membranes were prepared by non-covalently immobilizing the organic nanostructured molecule to a nitrocellulose membrane. Control membranes were also prepared by directly attaching the capture molecule to the nitrocellulose membrane in the absence of the organic nanostructured molecule.

A lateral flow type kit was prepared using these membranes. Various concentrations of cTnI antigen in human serum were prepared as described above. To each test kits, a 100 μL of the sample was placed and sandwiched with cTnI specific binding detection antibody (4T21 clone 19C7, HyTest, Finland) polymerized with fluorescent (FSD™ 647, 650 nm maximum excitation, 665 nm maximum emission, BioActs, Korea). The fluorescence signal was detected using a laser diode (650 nm) and detecting 665 nm emission fluorescence using photodiode equipped with an optical filter with wavelength cut-off below 660 nm. This procedure was repeated eight times per nitrocellulose membrane.

Standard curve for the concentration of target material (cTnI) was obtained by integrating the area of the control and test line area and converting the test line area integration value into the T/C ratio. CV (%) was calculated using the average values and standard deviations of the converted concentrations. See FIG. 5. A trend line in the CV graph of the sample concentration was made in the form of exponentiation, and the concentration at CV 10% was calculated. When the organic nanostructured molecule with an aldehyde and an epoxide linear region terminal end function group were used, the results showed improvement in quantitative assay reliability.

Figure 5:
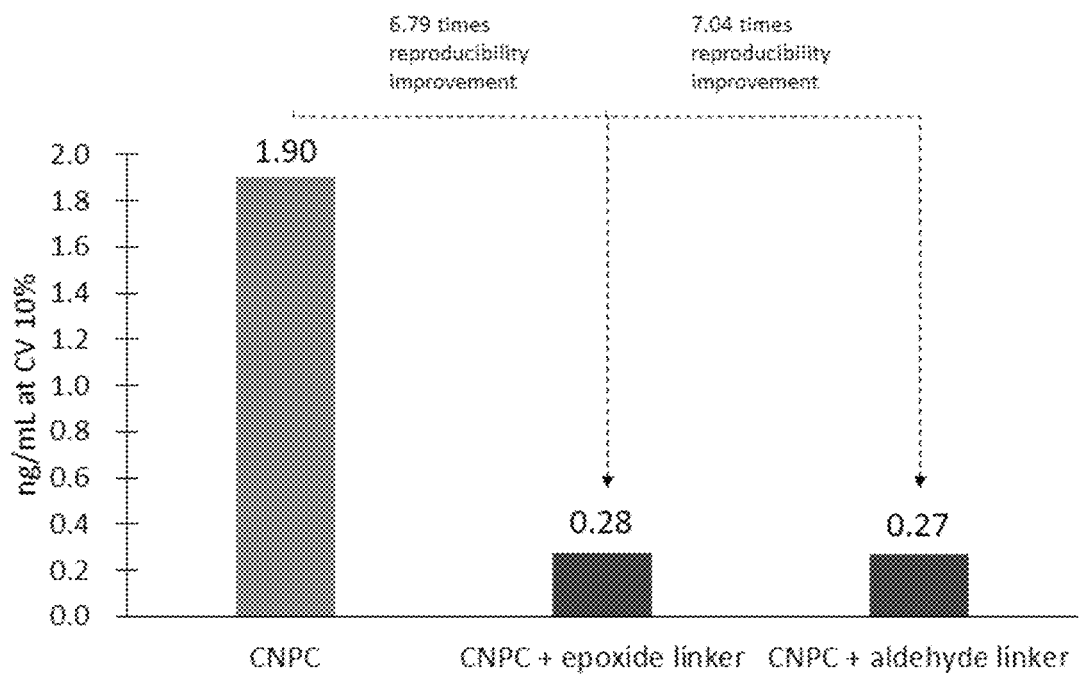
FIG. 5 is a graph showing the reproducibility results of the epoxide and aldehyde functional groups of the organic nanostructure according to example 2 at concentration of CV 10% and the reproducibility enhancement magnification.

The CV 10% for the control nitrocellulose membrane, nitrocellulose membrane with an organic nanostructured molecule having an epoxide linear region terminal end functional group, and nitrocellulose membrane with an organic nanostructured molecule having an aldehyde linear region terminal end function group was 1.90 ng/mL, 0.28 ng/mL, and 0.27 ng/mL, respectively. FIG. 5. This indicates that a nitrocellulose membrane with an organic nanostructured molecule has improved quantitative analysis regardless of the type of linear region terminal end functional group of the organic nanostructured molecule. FIG. 5.

Example 3

This example determines improvement in reproducibility of lateral flow assay kits having organic nanostructured compounds with a positive charge (MW 657.07, $C_{24}H_{52}Cl_3N_7O_7$) or a negative charge (MW 762.93, $C_{27}H_{41}K_3N_4O_{14}$).

An organic nanostructured molecule (MW 762.93, $C_{27}H_{41}K_3N_4O_{14}$) having a negative charge at the branched region terminal end and an organic nanostructured molecule having a positive charge (MR 657.07, $C_{24}H_{52}Cl_3N_7O_7$) were covalently attached to a capture molecule. Briefly, 4.1 molar equivalents of the organic nanostructured molecules having an epoxide linear region terminal end functional group was prepared with cTnI antibody as described above. Control nitrocellulose membranes were also prepared where the capture molecule was attached directed to the nitrocellulose membrane without the use of an organic nano structured molecule.

A lateral flow type kit was prepared using these membranes. Various concentrations of cTnI antigen in human serum were prepared as described above. To each assay test kits, a 100 μL of the sample was placed and sandwiched with cTnI specific binding detection antibody (4T21 clone 19C7, HyTest, Finland) polymerized with fluorescent (FSD™ 647, 650 nm maximum excitation, 665 nm maximum emission, BioActs, Korea). The fluorescence signal was detected using a laser diode (650 nm) and detecting 665 nm emission fluorescence using photodiode equipped with an optical filter with wavelength cut-off below 660 nm. This procedure was repeated eight times per nitrocellulose membrane.

Standard curve for the concentration of target material (cTnI) was obtained by integrating the area of the control and test line area and converting the test line area integration value into the T/C ratio. CV (%) was calculated using the average values and standard deviations of the converted concentrations. See FIG. 6. A trend line in the CV graph of the sample concentration was made in the form of exponentiation, and the concentration at CV 10% was calculated. When the organic nanostructured molecule with a positive branched region terminal end and a negative branched region terminal end were used, the results showed improvement in quantitative assay reliability.

Figure 6:
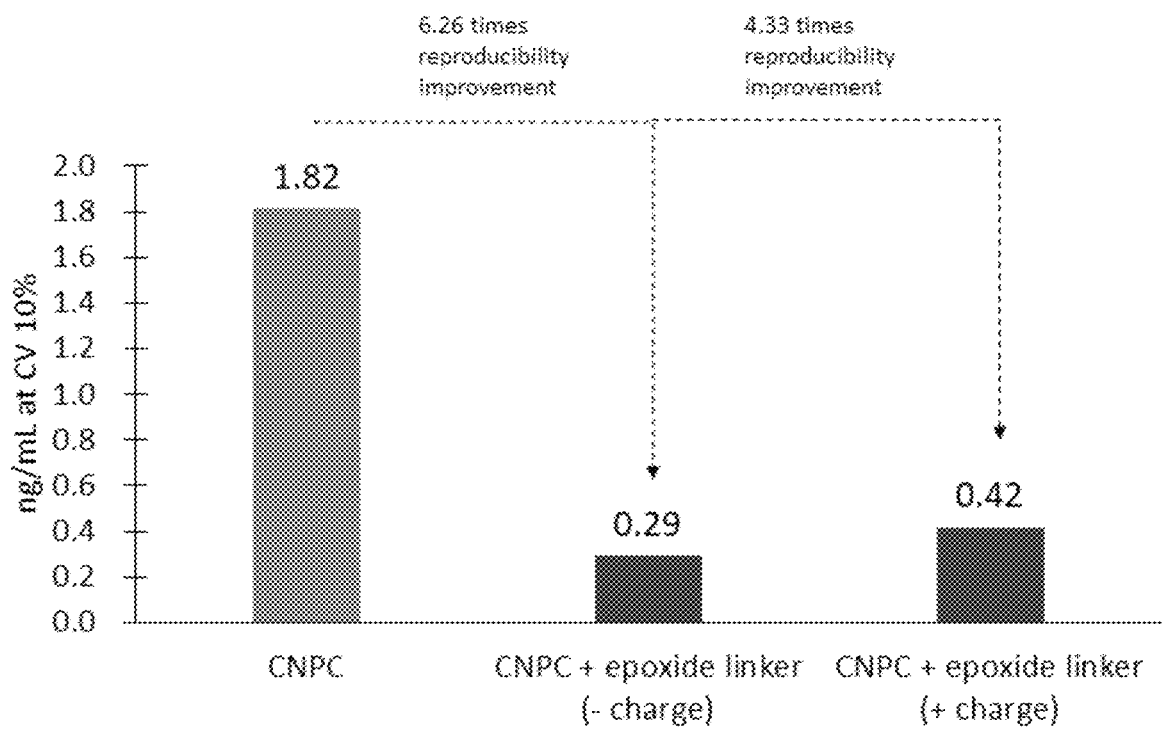
FIG. 6 is a graph showing the reproducibility of the organic nanostructure with the branched ends as negative charge or positive charge according to example 3 at concentration of CV 10% and the reproducibility enhancement magnification.

The CV 10% for the control nitrocellulose membrane, nitrocellulose membrane with an organic nanostructured molecule having a negative branched region terminal end, and nitrocellulose membrane with an organic nanostructured molecule having a positive branched region terminal end was 1.82 ng/mL, 0.29 ng/mL, and 0.42 ng/mL, respectively. FIG. 6. This is equivalent to improvement in quantitative assay reliability of 6.26 times and 4.33 times, respectively, for a negative branched region terminal end organic nanostructured molecule and a positive branched region terminal end organic nanostructured molecule, respectively. As can be seen, it appears a better quantitative improvement was obtained when the branched region terminal end of the organic nanostructured molecule is negatively charged. See FIG. 6.

Example 4

In this example, lateral flow type kits of having three (MW 762.93, $C_{27}H_{41}K_3N_4O_{14}$) and nine branched region terminal functional groups (MW 1949.41, $C_{66}H_{98}K_9N_7O_{38}$) were prepared and tested.

Figure 7:
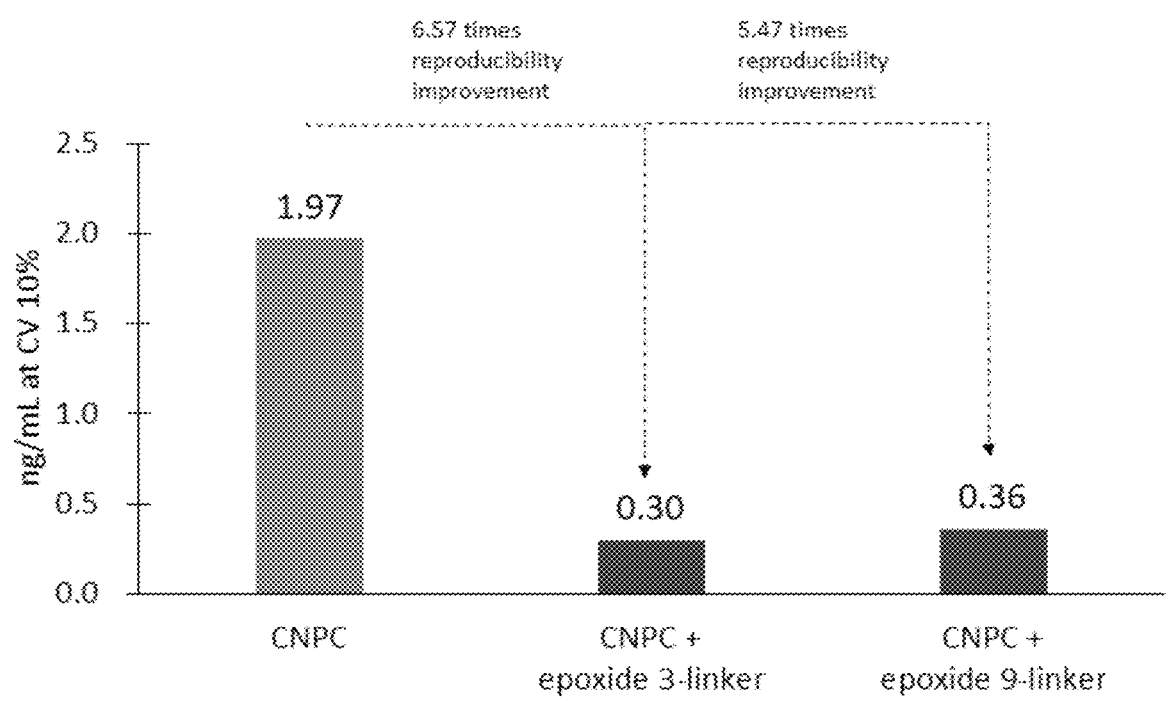
FIG. 7 shows the reproducibility results when the number of branching molecules of the organic nanostructure is 3 and 9 according to example 4 at concentration of CV 10% and the reproducibility enhancement magnification.

The corresponding assay test kits and the assay tests were conducted as described above. The CV 10% concentration for the control, organic nanostructured molecule having three branched region terminal functional groups, and organic nanostructured molecule having nine branched region terminal functional groups was 1.97 ng/mL, 0.30 ng/mL, and 0.36 ng/mL, respectively. See FIG. 7. This is equivalent to improvement in quantitative assay reliability of 6.57 times and 5.47 times, respectively, compared to the control group. FIG. 7.

Example 5

In this example, test kits were prepared by two different methods. The first method was a sequential method where an organic nanostructured molecule was attached first to a nitrocellulose membrane and a capture molecule was attached to the organic nanostructured molecule. The second method involved covalently linking a capture molecule to an organic nanostructured molecule prior to immobilizing the organic nanostructured molecule to a nitrocellulose membrane.

In the first method, 0.111 mM (4.1 equivalents relative to the capture molecule) of the organic nanostructured molecule (MW 762.93, $C_{27}H_{41}K_3N_4O_{14}$) was dispensed to a nitrocellulose membrane (CNPC, Advanced Microdevices, Inc.) at dispensing rate of 0.35 μL/cm to form a line. The resulting nitrocellulose membrane was dried at 40° C. in a relative humidity of 10% or less for about 10 minutes and then further dried at 60° C. under a relative humidity of 10% or less for 24 hours. The cTnI-specific capture antibody (0.027 mM, 0.35 μL/cm dispensing rate) was dispensed at the same position and dried at 40° C. at 10% relative humidity for about 10 minutes, and further dried at 60° C. under a relative humidity of 10% or less for 24 hours.

For the second method, 0.111 mol of the organic nanostructured molecule (FW 762.93, $C_{27}H_{41}K_3N_4O_{14}$, 4.1 mole equivalents relative to the capture molecule) was mixed with the capture molecule, i.e., cTnI antibody, (0.027 mM). The mixture was reacted for 3 hours with stirring at 37° C. The resulting reaction mixture was dispensed onto a nitrocellulose membrane (CNPC, Advanced Microdevices, India) at a dispensing rate of 0.35 μL/cm to form a line and dried at 40° C. in 10% relative humidity for about 10 minutes. The nitrocellulose membrane was further dried at 60° C. under a relative humidity of 10% or less for 24 hours.

Figure 8:
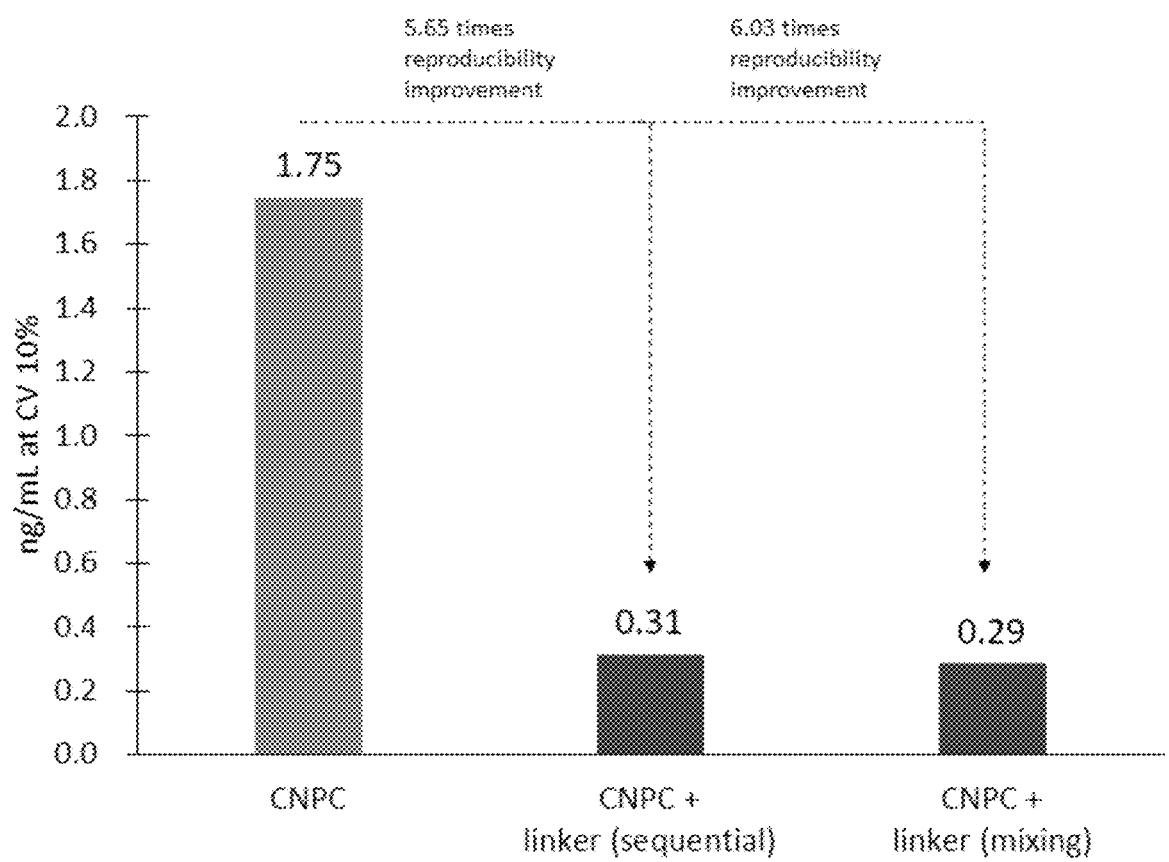
FIG. 8 is the reproducibility at concentration of CV 10% and the reproducibility enhancement, using sequential method and mixing method when combining organic nanostructure and the capturing material as example 5 shown.

Lateral flow type assay kits were prepared using the membranes prepared by the above two methods. And assay was conducted as described above. The CV 10% concentration of the control, the nitrocellulose membrane prepared by the first method, and the nitrocellulose membrane prepared by the second method was 1.75 ng/mL, 0.31 ng/mL and 0.29 ng/mL, respectively. See FIG. 8. This is equivalent to improvement in quantitative assay reliability of 5.65 times and 6.03 times, respectively, compared to the control group. FIG. 8.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A lateral flow assay kit for detecting a presence of a target molecule in a sample, said literal flow assay kit comprising a porous nitrocellulose membrane, wherein a surface of said porous nitrocellulose membrane comprises a non-covalently attached organic nanostructure compound comprising a plurality of terminal end moieties that are non-covalently attached to said nitrocellulose membrane surface, and wherein said organic nanostructure compound further comprises a covalently bound capture molecule, wherein said organic nanostructure comprises:
- a central atom;
- a branched region having said plurality of terminal end moieties that are non-covalently attached to the surface of said porous nitrocellulose membrane; and
- a single linear region having a covalently bound capture molecule on the terminal end of said linear region, wherein said capture molecule is adapted to selectively bind to a target material, and wherein said sample does not contain said nanostructure compound.

2. The lateral flow assay kit of claim 1, wherein said branched region of said organic nanostructure compound comprises at least three terminal end moieties that are non-covalently attached to the surface of said nitrocellulose membrane.

3. A method for producing a lateral flow assay kit comprising a porous nitrocellulose membrane adapted for detecting a presence of a target molecule in a sample, said method comprising:
   a) (A) non-covalently immobilizing an organic nanostructure on a surface of said nitrocellulose membrane, wherein said organic nanostructure comprises:
      (i) a central atom;
      (ii) a branched region having a plurality of terminal end moieties that are non-covalently attached to the surface of said porous nitrocellulose membrane; and
      (iii) a single linear region having a covalently bound capture molecule on a terminal end of said linear region, wherein said capture molecule is adapted to selectively bind to the target material when the target material is present in the sample; or
   (B) (i) immobilizing an organic nanostructure on a surface of said nitrocellulose membrane by a plurality of non-covalent attachments, wherein said organic nanostructure compound comprises:
      (a) a central atom;
      (b) a branched region having a plurality of terminal end moieties that are non-covalently attached to the surface of said porous nitrocellulose membrane; and
      (c) a single linear region comprising a terminal end having a functional group adapted for covalently attaching a capture molecule that is adapted to selectively bind to the target material when the target material is present in the sample; and
      (ii) reacting the capture molecule with the functional group of the terminal end of said linear region under conditions sufficient to produce a linear region of said organic nanostructure compound that comprises a covalently attached capture molecule; and
   b) producing the lateral flow kit using said nitrocellulose membrane.

4. A method for detecting a presence of a target molecule in a sample, said method comprising:
   (a) contacting a porous nitrocellulose membrane of a lateral flow kit of claim 1 with a sample under conditions sufficient to allow binding of the target material to a capture molecule that is present on a linear terminal end of said organic nanostructure compound when the target material is present in the sample, thereby forming a capture molecule-target material complex;
   (b) contacting a detecting material to the porous nitrocellulose membrane of said step (a), wherein said detecting material comprising a detection molecule that selectively binds to the capture molecule-target material complex when the capture molecule-target material complex is present; and
   (c) analyzing the porous nitrocellulose membrane of said step (b) to determine the presence of the target material in the sample.

5. The method of claim 4, wherein said analyzing comprises quantitative analysis, qualitative analysis or a combination thereof.

6. The method of claim 4, wherein each of the plurality terminal ends of the branched region of said organic nanostructure independently comprises a positive charge or a negative charge, thereby allowing non-covalent attachment of the branched region of said organic nanostructure to the surface of said porous nitrocellulose membrane.

7. The method of claim 4, wherein said detection molecule comprises an enzyme, a fluorophore, a magnetic particle, a nanoparticle, a metal particle, a nanofiber particle, or a combination thereof.

8. The method of claim 4, wherein said capture molecule is selected from the group consisting of an antigen, an antibody, DNA, RNA, PNA, aptamer, lipid, a hormone, an inorganic substance, a cell, a ligand, and a combination thereof.

9. The method of claim 4, wherein the sample is selected from the group consisting of a biological sample, a chemical sample, an environmental sample, and a food sample.

10. The method of claim 4, wherein the target material is selected from the group consisting of an antigen, an antibody, a peptide, a DNA, an RNA, a PNA, an aptamer, a ligand, a metabolite, a toxic compound, a lipid, a hormone, bacteria, virus, an exosome, a macro-vesicle, a micro-vesicle, a cell, and a combination thereof.

11. The method of claim 4, wherein said organic nanostructure compound is of the formula 1 or 2:

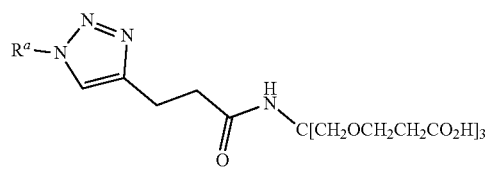

Formula 1

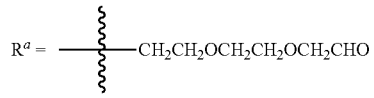

Formula 2

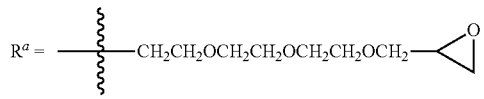

12. An assay kit for analyzing a presence of a target material in a sample, said assay kit comprising a lateral flow assay kit of claim 1.

13. The assay kit of claim 12, wherein said capturing molecule is selected from the group consisting of an antigen, an antibody, a DNA, an RNA, a PNA, an aptamer, a lipid, a hormone, an inorganic substance, a cell, a ligand, a peptide, and a combination thereof.

14. The assay kit of claim 12, wherein said assay kit is a lateral flow type.

15. A porous nitrocellulose membrane comprising a surface and a non-covalently immobilized organic nanostructured molecule of the formula:

Formula A

L—$Q^1$—$(T)_{a1}$ wherein

L is a linear region moiety of said organic nanostructured molecule comprising a triazole moiety, wherein L further comprises:
  (i) a linear region terminal functional group adapted for covalently attaching a capture molecule that is adapted to selectively bind to a target molecule, or
  (ii) a covalently attached capture molecule that is adapted to selectively bind to a target molecule;

$Q^1$ is a central atom of said organic nanostructured molecule having an oxidation state of at least 3;

$a^1$ is an integer from 2 to the oxidation state of $Q^1$-1; and each T is independently a branched terminal region moiety of said organic nanostructured molecule comprising a branched terminal region functional group that is adapted to non-covalently attaching said organic nanostructured molecule to said porous nitrocellulose membrane;

and wherein said organic nanostructured molecule is non-covalently attached to said porous nitrocellulose membrane by a plurality of said branched terminal region functional groups.

16. The porous nitrocellulose membrane of claim 15, wherein said organic nanostructured molecule is of the formula:

IA

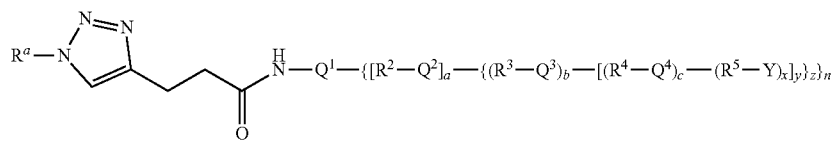

wherein
each of a, b, and c is independently 0 or 1;
x is 1 when c is 0 or when c is 1, x is an integer from 1 to the oxidation state of $Q^4$-1;
y is 1 when b is 0 or when b is 1, y is an integer from 1 to the oxidation state of $Q^3$-1;
z is 1 when a is 0 or when a is 1, z is an integer from 1 to the oxidation state of $Q^2$-1;
n is an integer from 1 to the oxidation state of $Q^1$-1;
L and $Q^1$ are as defined in claim 15;
each of $Q^2$, $Q^3$ and $Q^4$ is independently a branch atom having the oxidation state of at least 3;
each of $R^2$, $R^3$, $R^4$, and $R^5$ is independently a linker; and
Y is said branched terminal region functional group, provided the product of n, x, y, and z is at least 3.

17. The porous nitrocellulose membrane of claim 16, wherein said organic nanostructured molecule is of the formula:

IB

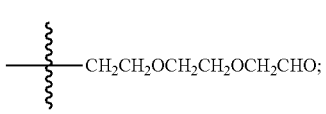

wherein
$Q^1$, $Q^2$, $Q^3$, $Q^4$, $R^2$, $R^3$, $R^4$, $R^5$, Y, a, b, c, x, y, z, and n are as defined in claim 16;
$R^a$ is selected from the group consisting of:

(Formula L1)

(Formula L2)

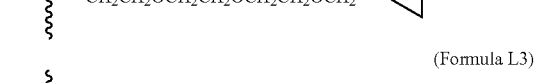

(Formula L3)

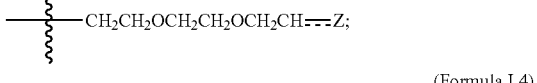

(Formula L4)

a combination thereof,
wherein
a dotted line represents optional double bond;
Z is the capture molecule that is adapted to selectively bind to a target molecule, and wherein said Z is covalently attached using the aldehyde functional group of compound of Formula 1 or the epoxide functional group of compound of Formula 2.
18. The porous nitrocellulose membrane of claim 17, wherein said organic nanostructured molecule is of the formula:
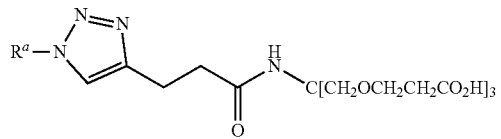
IC
wherein $R^a$ is as defined in claim 17.
* * * * *